United States Patent [19]

Kubo et al.

[11] 4,198,512
[45] Apr. 15, 1980

[54] 1-OXO-1,2-DIHYDROISOQUINOLINE DERIVATIVES

[75] Inventors: Kazuo Kubo, Urawa; Noriki Ito, Iwatsuki; Isao Souzu, Urawa; Yasuo Isomura, Yokohama; Hiroshige Homma, Omiya, all of Japan

[73] Assignee: Yamanouchi Pharmaceutical Co., Ltd., Tokyo, Japan

[21] Appl. No.: 925,217

[22] Filed: Jul. 17, 1978

[30] Foreign Application Priority Data

Jul. 22, 1977 [JP] Japan .................................. 52/88064

[51] Int. Cl.² .................. C07D 217/24; A61K 31/47
[52] U.S. Cl. ...................................... 546/142; 424/258
[58] Field of Search ......................... 546/142; 424/258

[56] References Cited

FOREIGN PATENT DOCUMENTS 1394700  5/1975  United Kingdom ..................... 546/142

OTHER PUBLICATIONS

Takaki et al., J. Org. Chem., vol. 43(3), pp. 402–405 (1978).

Primary Examiner—Glennon H. Hollrah
Assistant Examiner—D. Rivers
Attorney, Agent, or Firm—Burgess, Ryan and Wayne

[57] ABSTRACT

Novel 1-oxo-1,2-dihydroisoquinoline compounds of the formula

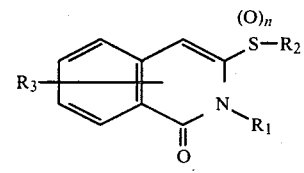

wherein $R_1$ represents a lower alkyl group or a phenyl lower alkyl group; $R_2$ represents a lower alkyl group; $R_3$ represents a hydrogen atom, a lower alkanoyl group, a lower alkyl group or a hydroxy lower alkyl group; and n is 0, 1 or 2 and the pharmacologically acceptable non-toxic salts thereof.

The compounds of this invention are strong analgesic anti-inflammatory agents.

9 Claims, No Drawings

1-OXO-1,2-DIHYDROISOQUINOLINE DERIVATIVES

DETAILED DESCRIPTION OF THE INVENTION

This invention relates to novel isoquinoline compounds. More particularly, the invention relates to 1-oxo-1,2-dihydroisoquinoline compounds of the formula I

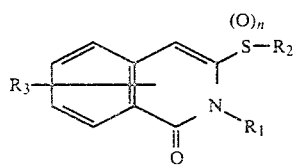

wherein $R_1$ represents a lower alkyl group or a phenyl lower alkyl group; $R_2$ represents a lower alkyl group; $R_3$ represents a hydrogen atom, a lower alkanoyl group, a lower alkyl group or a hydroxyl lower alkyl group; and n is 0, 1 or 2; said $R_3$ may be at any position of the 4-, 5-, 6-, 7- and 8- positions of the isoquinoline ring, and the pharmacologically acceptable non-toxic salts thereof.

The compounds of this invention of formula I possess a very strong anti-inflammatory activity together with a strong analgesic activity, and hence are the novel useful compounds which are expected to be strong analgesic anti-inflammatory agents.

Now, the term "lower" used throughout the specification and the claims of this invention means a straight or branched carbon chain having 1-6 carbon atoms. Practically, "lower alkyl groups" include a methyl group, ethyl group, propyl group, isopropyl group, n-butyl group, isobutyl group, sec-butyl group, tert-butyl group, amyl group, isoamyl group, n-hexyl group, etc. and "phenyl lower alkyl groups" include a benzyl group and a phenethyl group, etc.; and "lower alkanoyl groups" include a formyl group, acetyl group, propionyl group, butyryl group, isobutyryl group, etc.

The compounds of this invention of formula I have the feature in their chemical structure in that each compound has a lower alkyl group or a phenyl lower alkyl group at the 2-position (N-position) of the 1-oxo-1,2-dihydroquinoline and have

wherein $R_2$ and n have the same significance as in formula I, (e.g., a lower alkylthio group, a lower alkylsulfinyl group or a lower alkylsulfonyl group) at the 3-position.

1-Oxo-1,2-dihydroisoquinoline is also called "1(2H)-isoquinolone" or "isocarbostyril" and many derivatives thereof are known but the 1-oxo-1,2-dihydroisoquinoline compounds of this invention of formula I herein are not yet known.

Preferred examples of the compounds of this invention are;
2-methyl-3-methylthio-1-oxo-1,2-dihydroisoquinoline,
2-methyl-3-methylsulfinyl-1-oxo-1,2-dihydroisoquinoline,
2-methyl-3-methylsulfonyl-1-oxo-1,2-dihydroisoquinoline,
2-ethyl-3-methylthio-1-oxo-1,2-dihydroisoquinoline,
2-ethyl-3-methylsulfonyl-1-oxo-1,2-dihydroisoquinoline,
2,4-dimethyl-3-methylsulfonyl-1-oxo-1,2-dihydroisoquinoline,
2,7-dimethyl-3-methylsulfonyl-1-oxo-1,2-dihydroisoquinoline, and
4-formyl-2-methyl-3-methylsulfonyl-1-oxo-1,2-dihydroisoquinoline.

As the pharmacologically acceptable non-toxic salts of the compounds of this invention, there are illustrated the addition salts of an acid such as hydrochloric acid, hydrobromic acid, sulfuric acid, nitric acid, phosphoric acid, etc.

The compounds of this invention of formula I herein can be prepared by the following processes.

Production process 1

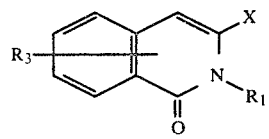

(1) $M-S-R_2$ (2) Oxidation, if necessary,

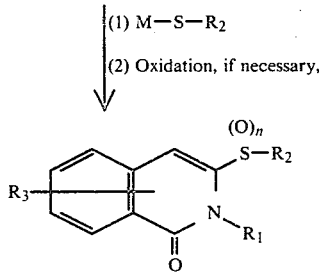

in the above formulae, X represents a halogen atom; M represents an alkali metal; and $R_1$, $R_2$, $R_3$ and n have the same significance as in formula I.

This reaction is performed by reacting the compound of formula II with the alkali metal alkylsulfide shown by formula $M-S-R_2$ and then, if necessary, oxidizing the reaction product.

Examples of the alkali metal alkylsulfide used in the above reaction are sodium methylsulfide, potassium methylsulfide, sodium ethylsulfide, sodium propylsulfide, etc.

The reaction of the compound of formula II and the sulfide is performed in an organic solvent such as tetrahydrofuran, ethanol, dimethylformamide, ethylene glycol, dimethyl ether, etc. The reaction is promoted when carried out under heating and is usually performed under refluxing. Thus, the compounds of this invention of formula I wherein n is 0, can be obtained.

The compounds of this invention of formula I wherein n is 1 or 2 can be obtained by oxidizing the compound of formula I wherein n is 0 with a proper oxidizing agent. The oxidation can be performed in an acid solvent such as acetic acid using an oxidizing agent such as hydrogen peroxide. As hydrogen peroxide, a 10-40% hydrogen peroxide solution is usually used. By properly controlling the oxidation conditions, particularly the reaction period of time, the reaction temperature, and the amount of the oxidizing agent, the sulfinyl compounds of formula I wherein n is 1 or the sulfonyl compounds of formula I wherein n is 2, can be efficiently obtained.

Production process 2

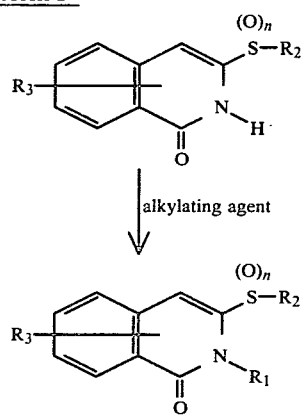

in the above formulae, $R_1$, $R_2$, $R_3$ and n have the same significance as in formula I previously indicated.

The process is performed by reacting a compound of formula III and an alkylating agent in a solvent such as methanol, acetone, dimethylformamide, etc. Examples of the alkylating agent used in the reaction are alkyl halides (or phenylalkyl halides) such as methyl iodide, ethyl bromide, benzyl bromide, phenethyl iodide, etc., and dialkyl sulfates such as dimethyl sulfate, diethyl sulfate, etc.

Furthermore, the compounds of formula I wherein $R_3$ is a formyl group can also be prepared by reacting a compound of formula I wherein $R_3$ is a hydrogen atom with a Vilsmeier reagent, that is, the complex of dimethylformamide and phosphoryl chloride and then hydrolyzing the reaction product.

Also, the compound of formula I wherein $R_3$ is a hydroxymethyl group can be prepared by reducing a compound of formula I wherein $R_3$ is a formyl group, in a conventional manner.

Moreover, the compounds of formula I wherein n is 1 (sulfinyl compound) or n is 2 (sulfonyl compound), which can be prepared by the above-mentioned process, can also be prepared by oxidizing a compound of formula I wherein n is 0 by the same manner as described in Production process 1.

The compounds of this invention shown by formula I thus prepared may be isolated and purified by an ordinary chemical operation such as concentration, recrystallization, column chromatography, etc.

Then, the results of the following therapeutical experiments show the excellent therapeutical activities of the compounds of this invention.

(a) Carrageenin-induced edema

Male Wister rats (weighing 130–170 g.), one group being 6 rats, fasted overnight were used. According to Winter's method [Proc. Soc. Exp. Biol. Med., 111,544 (1962)], 0.1 ml. of 1% carrageenin [Iwai Kagaku Yakuhin K.K. Seakem] suspension in 0.9% saline was injected into the planter tissue of the left hind paw. After 3 hours, each rat was sacrificed by chloroform and the hind paw was cut and weighed immediately. By using the value obtained by subtracting the weight of the untreated hind paw from the weight of the hind paw having injected therein the carrageenin as the weight of edema, the inhibitory ratio of the sample administered rat groups to control groups was calculated. The sample was orally administered before one hour of the injection of Carrageenin. The results obtained are shown in Table 1.

(b) Whittle's method (British J. Pharmacol.; 22, 246–253 (1964))

Male ICR-Mice (weighting 25–35 g.), one group being 12 mice, fasted overnight were used in this test. The sample was orally administered, and 20 minutes after, 5 ml./Kg. of 0.4% Evance blue was injected intravenously and 10 minutes thereafter, 10 ml./Kg. of 0.6% acetic acid was injected intraperitoneally. The number of writhings after 20 minutes following the administration of acetic acid was recorded and after an additional 10 minutes, the mice were killed by dislocation of the neck, the dye leaked in the abdominal cavity was washed out with 5 ml. of 0.9% saline to make the total amount 10 ml., and thereafter furs, blood corpuscles, etc., intermingled were removed by centrifugal separation at 3,000 r.p.m. for 5 minutes. Furthermore, to prevent turbidity caused by protein, 0.1 ml. of an aqueous 0.1 normal sodium hydroxide was added and then the absorbance at 590 nm was measured. The inhibition ratio of the sample administered rat groups to control groups was calculated. The results are shown in Table 2.

In addition, the test samples used in the aforesaid tests (a) and (b) were prepared by suspending the test compounds in an aqueous 0.5% methyl cellulose solutions.

Table 1

| | (Carrageenin-induced edema) | | |
|---|---|---|---|
| | Sample | Dose (mg/kg) | Inhibition (%) |
| Compound of this invention | Ex. 1 | 100 | 57.3 |
| | Ex. 2 | 50 | 38.5 |

Table 1-continued
(Carrageenin-induced edema)

| Sample | | Dose (mg/kg) | Inhibition (%) |
|---|---|---|---|
| Ex. 4 | 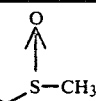 | 50<br>100 | 55.8<br>68.2 |
| Ex. 5 | | 50<br>100 | 50.7<br>68.1 |
| Known compound | Phenyl butazone | 50<br>100 | 44.5<br>51.2 |

Table 2
(Whittle's method)

| Sample | | Writhing<br>50 mg/kg P.O. | Permeability<br>50 mg/kg P.O. |
|---|---|---|---|
| Compound of this invention | Ex. 4 | 39.7 | 42.8 |
| | Ex. 5 | 45.8 | 47.1 |
| Known compound | Aminopyrine | 58.1 | 41.7 |

From the test results by the aforesaid Carrageenin-induced edema and Wittle's method, it is clear that the compounds I of this invention have excellent anti-inflammatory activity and excellent analgesic activity.

The clinical doses of the compounds I of this invention are usually 100–1,000 mg., preferably 150–600 mg. per day for an adult and the medicament is administered 2–3 times per day. The doses are properly controlled according to the condition and age of the patient.

The compounds of this invention are administered as various forms such as agents for oral administration, injections, suppositories for rectal administration, medicines for topical application, etc.

The medicaments of this invention are used as compositions prepared by blending with conventional pharmaceutical carriers or excipients using ordinary methods. The tablets, capsules, granules, powders, etc., of the compounds of this invention for oral administration may contain a pharmaceutical excipient generally used in the art such as calcium carbonate, calcium phosphate, starch, sucrose, lactose, talc, magnesium stearate, gelatin, polyvinyl pyrrolidone, gum arabic, sorbitol, microcrystalline cellulose, polyethylene glycol, silica, sodium laurylsulfate, etc. Moreover, the tablets may be coated by procedures well known in the art.

Furthermore, the liquid formulations for oral administration may be an aqueous or oily suspension, a syrup, an elixir, etc., and are prepared by a conventional method.

Suppositories for rectal use are used and they may contain a formulation carrier well known in the art, such as polyethylene glycol, lanolin, cacao butter, Witepsol ® (made by Dynamite Nobel Co.), etc.

Then, examples of the formulations of the medicaments of this invention are shown below:

Formulation example 1:

Tablets containing a compound of this invention shown by formula I, the weight of one tablet being 300 mg.

| | |
|---|---|
| Compound of formula I | 1,000 g. |
| Lactose | 1,200 g. |
| Starch | 770 g. |
| Magnesium stearate | 30 g. |

A 10% starch paste was prepared using a part of starch described above and after adding the starch paste as a binder to a mixture of the compounds of formula I, lactose and the remaining starch, the resultant mixture was granulated by a conventional manner. Then, magnesium stearate was added to the granules and the mixture was molded into 10,000 tablets each having a diameter of 9.5 mm. and a weight of 300 mg. The active component was 100 mg./tablet.

Formulation example 2:

Capsules containing a compound I of this invention, the weight of one capsule being 300 mg.

| Compound of formula I | 1,000 g. |
|---|---|
| Lactose | 1,200 g. |
| Starch | 770 g. |
| Magnesium stearate | 30 g. |

After mixing well 1,000 g. of a compound of formula I, 1,200 g. of lactose, 770 g. of starch, and 30 g. of magnesium stearate, the mixture was filled in 10,000 capsules. The weight of each capsule filled with the mixture was 300 mg. The active component was 100 mg./capsule.

EXAMPLE 1

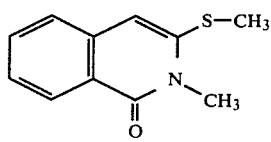

In 20 ml. of dimethylformamide, 5 g. of 3-chloro-2-methyl-1-oxo-1,2-dihydroisoquinoline and 7.5 g. of an aqueous solution of 20% sodium methylsulfide were refluxed for 1.5 hours. To the reaction mixture was added 50 ml. of water and the product was extracted with 50 ml. of ethyl acetate. The extract was washed with water, dried over anhydrous sodium sulfate, and then the solvent was distilled off under reduced pressure. The crude crystals thus obtained were recrystallized from cyclohexane with the addition of activated carbon to provide 3.8 g. of 2-methyl-3-methylthio-1-oxo-1,2-dihydroisoquinoline.

Melting point 83°–85° C.

| Elemental analysis for $C_{11}H_{11}NOS$: | | | |
|---|---|---|---|
| | C | H | N |
| Found: | 64.69% | 5.17% | 6.91% |
| Calculated: | 64.36% | 5.40% | 6.82 |

EXAMPLE 2

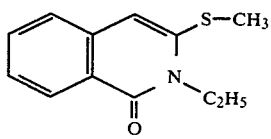

By following the same procedure as in Example 1 using 0.6 g. of 3-chloro-2-ethyl-1-oxo-1,2-dihydroisoquinoline and 0.8 g. of an aqueous solution of 20% sodium methylsulfide, 0.31 g. of 2-ethyl-3-methylthio-1-oxo-1,2-dihydroisoquinoline was obtained (recrystallized from cyclohexane).

Melting point 80°–82° C.

| Elemental analysis for $C_{12}H_{13}NSO$: | | | |
|---|---|---|---|
| | C | H | N |
| Found: | 65.46% | 5.85% | 6.45% |
| Calculated: | 65.72% | 5.97% | 6.39% |

EXAMPLE 3

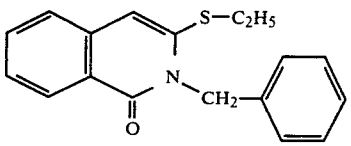

By following the same procedure as in Example 1 using 0.5 g. of 2-benzyl-3-chloro-1-oxo-1,2-dihydroisoquinoline and 0.6 g. of an aqueous solution of 20% sodium ethylsulfide, 0.37 g. of 2-benzyl-3-ethylthio-1-oxo-1,2-dihydroisoquinoline was obtained (recrystallized from cyclohexane).

Melting point 79°–80° C.

| Elemental analysis for $C_{18}H_{17}NSO$: | | | |
|---|---|---|---|
| | C | H | N |
| Found: | 73.39% | 5.88% | 4.38% |
| Calculated: | 73.19% | 5.80% | 4.74% |

EXAMPLE 4

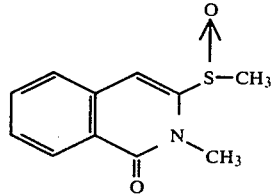

In 8 ml. of acetic acid was dissolved 1 g. of 2-methyl-3-methylthio-1-oxo-1,2-dihydroisoquinoline and after adding 0.65 g. of 30% hydrogen peroxide solution to the solution, the mixture was allowed to stand overnight. Then, after adding an aqueous solution of sodium hydrogensulfite to the mixture to remove excessive hydrogen peroxide, the reaction mixture was concentrated under reduced pressure. To the residue was added 10 ml. of water and the crystals formed were recovered by filtration, dried, and then recrystallized from methanol to provide 0.7 g. of 2-methyl-3-methylsulfinyl-1-oxo-1,2-dihydroisoquinoline.

Melting point 157°–159° C.

| Elemental analysis for $C_{11}H_{11}NO_2S$: | | | |
|---|---|---|---|
| | C | H | N |
| Found: | 59.54% | 4.78% | 6.51% |
| Calculated: | 59.71% | 5.01% | 6.33% |

EXAMPLE 5

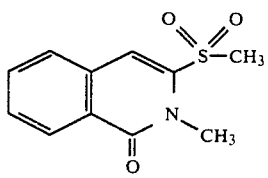

In 8 ml. of acetic acid was dissolved 1 g. of 2-methyl-3-methylthio-1-oxo-1,2-dihydroisoquinoline and after adding 1.4 g. of 30% hydrogen peroxide solution, the mixture was refluxed for 2.5 hours. To the reaction mixture thus obtained was added 15 ml. of water and the crystals formed were recovered by filtration and recrystallized from ethanol to provide 0.6 g. of 2-methyl-3-methylsulfonyl-1-oxo-1,2-dihydroisoquinoline.

Melting point 179°–180° C.

| Elemental analysis for $C_{11}H_{11}NO_3S$ | | | |
|---|---|---|---|
| | C | H | N |
| Found: | 55.59% | 4.43% | 5.79% |
| Calculated: | 55.68% | 4.97% | 5.90% |

EXAMPLE 6

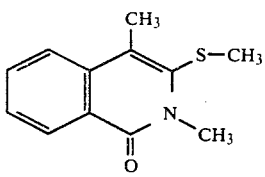

A mixture of 1.8 g. of 3-chloro-2,4-dimethyl-1-oxo-1,2-dihydroisoquinoline, 2.6 ml. of an aqueous solution of 20% sodium methylsulfide, and 5.2 ml. of dimethylformamide was heated to 80°–90° C. for 4 hours. The reaction mixture was cooled and the crystals formed were recovered by filtration and recrystallized from a mixture of dimethylformamide and water to provide 1.7 g. of 2,4-dimethyl-3-methylthio-1-oxo-1,2-dihydroisoquinoline.

Melting point 101°–103° C.

| Elemental analysis for $C_{12}H_{13}NOS$: | | | | |
|---|---|---|---|---|
| | C | H | N | S |
| Found: | 65.42% | 5.82% | 6.21% | 14.62% |
| Calculated: | 65.72% | 5.97% | 6.39% | 14.62% |

EXAMPLE 7

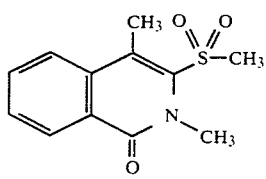

A mixture of 450 mg. of 2,4-dimethyl-3-methylthio-1-oxo-1,2-dihydroisoquinoline, 10 ml. of acetic acid, and 0.4 ml. of 30% hydrogen peroxide solution was heated to 100° C. for 3 hours. The reaction product formed was cooled and then poured into cold water. The crystals formed were recovered by filtration and recrystallized from ethanol to provide 150 mg. of 2,4-dimethyl-3-methylsulfonyl-1-oxo-1,2-dihydroisoquinoline.

Melting point 148°–150° C.

| Elemental analysis for $C_{12}H_{13}NO_3S$: | | | | |
|---|---|---|---|---|
| | C | H | N | S |
| Found: | 57.13% | 5.19% | 5.36% | 12.68% |
| Calculated: | 57.35% | 5.21% | 5.57% | 12.76% |

EXAMPLE 8

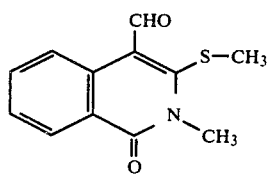

To a mixture of 3 g. of dimethylformamide and 20 ml. of chloroform was added dropwise 3 g. of phosphorus oxychloride under ice-cooling and then the mixture thus obtained was stirred for one hour at room temperature. Then, 3 g. of 2-methyl-3-methylthio-1-oxo-1,2-dihydroisoquinoline was added to the mixture and the resultant mixture was refluxed for 4 hours. The reaction mixture thus obtained was concentrated and the residue formed was dissolved in 30 ml. of water. Then, the solution was alkalified by the addition of potassium carbonate, whereby crystals were precipitated. The crude crystals were recovered by filtration and recrystallized from ethanol to provide 2.3 g. of 4-formyl-2-methyl-3-methylthio-1-oxo-1,2-dihydroisoquinoline.

Melting point 152°–153° C.

| Elemental analysis for $C_{12}H_{11}NO_2S$: | | | |
|---|---|---|---|
| | C | H | N |
| Found: | 61.79% | 4.65% | 6.25% |
| Calculated: | 61.78% | 4.75% | 6.00% |

EXAMPLE 9

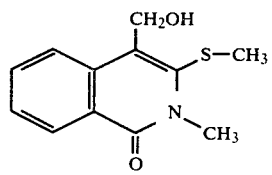

In 20 ml. of methanol was suspended 0.5 g. of 4-formyl-2-methyl-3-methylthio-1-oxo-1,2-dihydroisoquinoline and when 0.08 g. of sodium borohydride was added to the suspension followed by stirring, the dihydroisoquinoline was dissolved in methanol after 2 or 3 minutes. The reaction mixture was concentrated under reduced pressure and the crystals formed were washed with 10 ml. of water and recrystallized from ethanol to provide 0.4 g. of 4-hydroxymethyl-2-methyl-3-methylthio-1-oxo-1,2-dihydroisoquinoline.

Melting point 165°–167° C.

| Elemental analysis for $C_{12}H_{13}NO_2S$: | | | |
| --- | --- | --- | --- |
| | C | H | N |
| Found: | 61.15% | 5.51% | 5.80% |
| Calculated: | 61.25% | 5.57% | 5.95 |

What is claimed is:

1. 1-Oxo-1,2-dihydroisoquinoline compounds of the formula

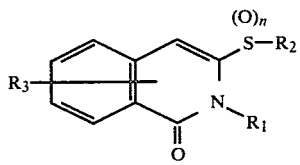

wherein $R_1$ represents a lower alkyl group or a pheny lower alkyl group; $R_2$ represents a lower alkyl group; $R_3$ represents a hydrogen atom, a lower alkanoyl group, a lower alkyl group or a hydroxy lower alkyl group; and n is 0, 1 or 2 and the pharmacologically acceptable non-toxic salts thereof.

2. A compound according to claim 1 which is 2-Methyl-3-methylsulfonyl-1-oxo-1,2-dihydroisoquinoline.

3. A compound according to claim 1 which is 2-Methyl-3-methylsulfinyl-1-oxo-1,2-dihydroisoquinoline.

4. A compound according to claim 1 which is 2-Methyl-3-methylthio-1-oxo-1,2-dihydroisoquinoline.

5. A compound according to claim 1 which is 2-ethyl-3-methylthio-1-oxo-1,2-dihydroisoquinoline.

6. A compound according to claim 1 which is 2-ethyl-3-methylsulfonyl-1-oxo-1,2-dihydroisoquinoline.

7. A compound according to claim 1 which is 2,4-dimethyl-3-methylsulfonyl-1-oxo-1,2-dihydroisoquinoline.

8. A compound according to claim 1 which is 2,7-dimethyl-3-methylsulfonyl-1-oxo-1,2-dihydroisoquinoline.

9. A compound according to claim 1 which is 4-formyl-2-methyl-3-methylsulfonyl-1-oxo-1,2-dihydroisoquinoline.